Figure 1:
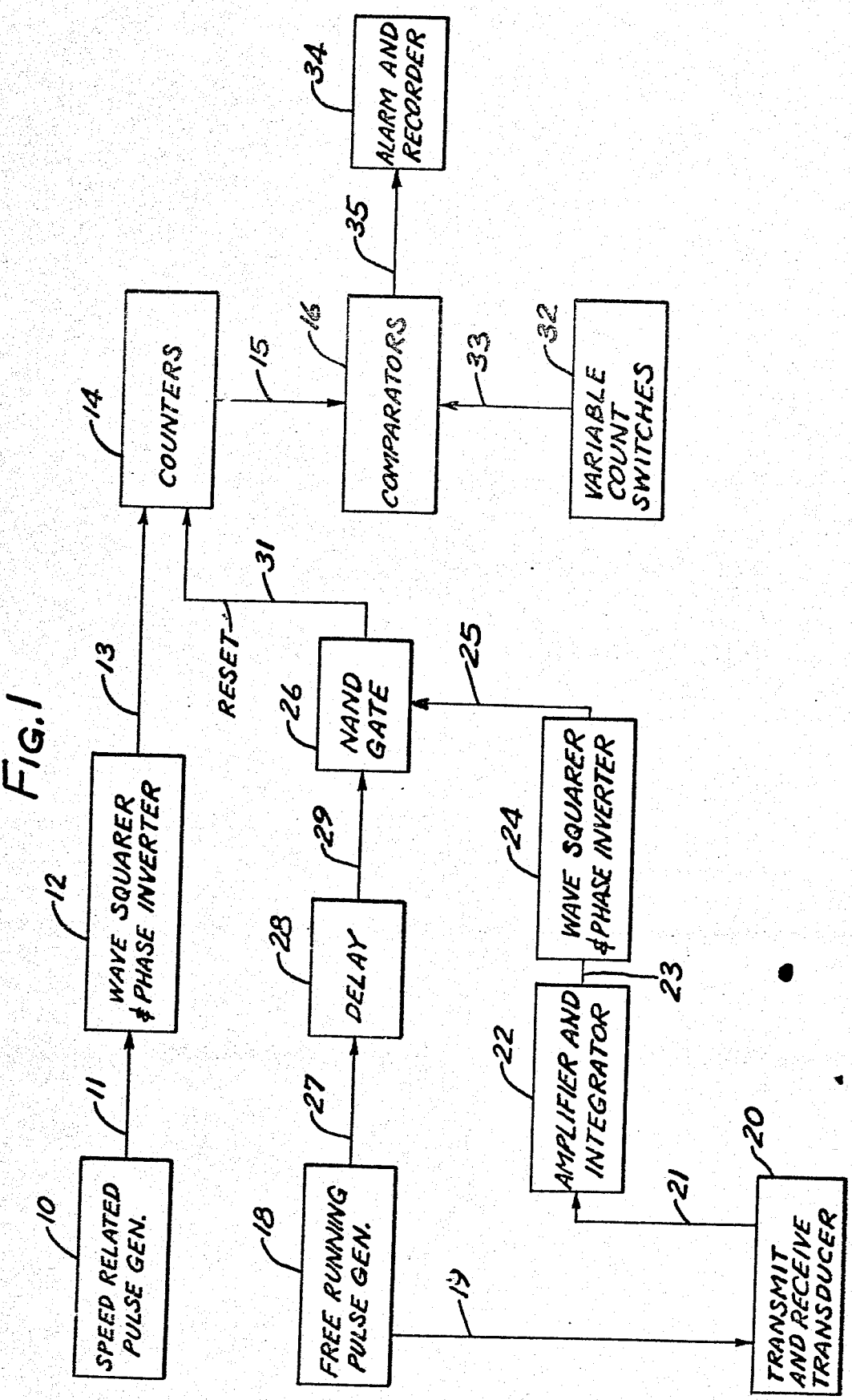

[11] 4,004,455
[45] Jan. 25, 1977

McKee et al.

[54] FLAW DETECTING APPARATUS FOR RAILROAD RAILS AND THE LIKE

[75] Inventors: Chester W. McKee, Flossmoor; C. Glenn Henderson, Ottawa, both of Ill.

[73] Assignee: Teleweld, Inc., Streator, Ill.

[22] Filed: May 23, 1975

[21] Appl. No.: 580,158

[52] U.S. Cl. .................................................. 73/67.9
[51] Int. Cl.² ............................................. G01N 29/04
[58] Field of Search ............ 73/67.9, 67.8 R, 67.8 S, 73/67.7, 67.5 R, 71.5 US

[56] References Cited
UNITED STATES PATENTS

| | | | |
|---|---|---|---|
| 2,736,193 | 2/1956 | Van Valkenburg | 73/67.9 |
| 3,287,963 | 11/1966 | Stanya et al. | 73/67.9 |
| 3,354,700 | 11/1967 | Schindler | 73/67.9 |
| 3,415,110 | 12/1968 | Cowan | 73/67.8 S |

*Primary Examiner*—James J. Gill
*Assistant Examiner*—Stephen A. Kreitman
*Attorney, Agent, or Firm*—Fitch, Even, Tabin & Luedeka

[57] ABSTRACT

Apparatus is disclosed for use in detecting flaws in the bolt hole area of railroad rails and the like, and is adapted to detect and record the location of an oversized hole indicating a crack or the like. The apparatus utilizes an ultrasonic transducer detector which is actuated by a free running pulse generator, and includes a counter and associated circuitry which compares the time required for the pulse to travel through the rail with a preset time and, if the rail has no flaw, causes an output to be produced that is used to reset the counter. The counter is also triggered by a speed related pulse generator that effectively measures the distance traveled by the car along the rail and thereby measures the size of the flaw. A flaw exceeding a predetermined size which is approximately the diameter of bolt holes, will trigger an alarm and cause a recorder to be activated.

9 Claims, 2 Drawing Figures

FLAW DETECTING APPARATUS FOR RAILROAD RAILS AND THE LIKE

This invention generally relates to detection apparatus and, more specifically, to flaw detection apparatus for use in detecting flaws in the bolt hole area of railroad rails or the like.

There has been much activity in the development of apparatus and systems which will rapidly or automatically detect flaws in railroad rails or the like. Since the manual detection of rails is becoming increasingly prohibitive from an economic standpoint, the use of automatic or semiautomatic equipment that will detect flaws as a vehicle travels along the rail is quite desirable, if not essential in the maintenance and care of railroad track. Ultrasonic transducer detector apparatus are one type of apparatus that has experienced increased acceptance by the railroad industry in detecting flaws. This type of apparatus operates on the principle of introducing high frequency sound waves into the top of the rail and measuring the time period that is required for the sound wave to rebound from the bottom of the rail. In the event a flaw exists, the time period will be less because the sound wave need not travel as far, i.e., downwardly and return through the entire height of the rail. Since much of the existing railroad track still comprises predetermined lengths of rail that are bolted together, rather than being a "continuous" length by welding sections together, the detection of flaws in railroad rail is hampered due to the presence of the bolt holes themselves, since the holes will cause the high frequency sound wave to be reflected from the hole itself rather than the bottom of the rail and will thereby produce a signal falsely indicating the presence of a flaw such as a crack or the like. Moreover, it is well known that cracks often originate at the bolt hole itself which makes it important that the detection system be effective in detecting flaws at or near the bolt holes of the rails.

Accordingly, it is a primary object of the present invention to provide improved apparatus for detecting flaws, particularly in the bolt hole area of railroad rail or the like.

Yet another object of the present invention is to provide such an improved apparatus which is relatively easily fabricated from commercially available components.

Figure 2:
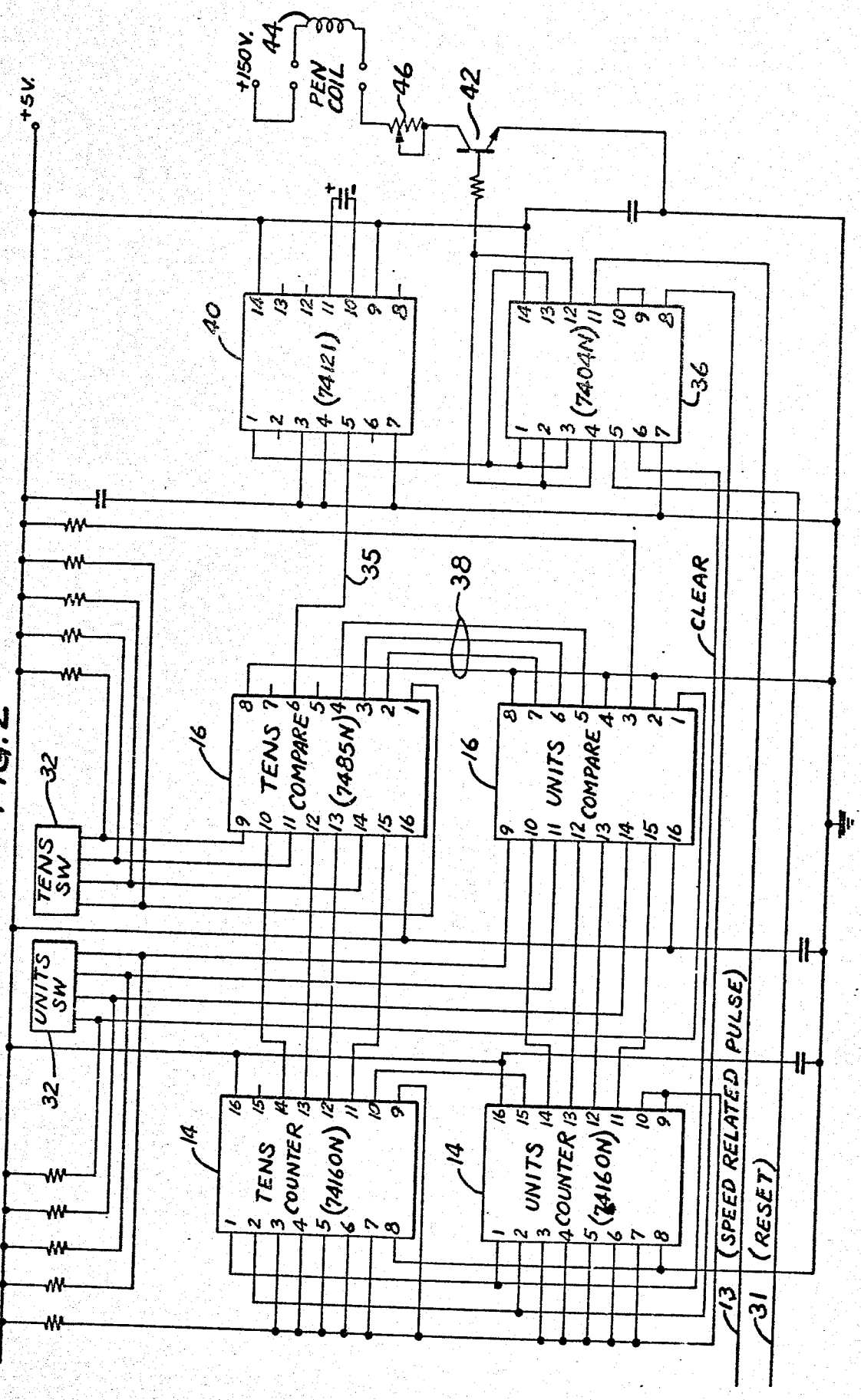

Other objects and advantages will become apparent upon reading the following detailed description, while referring to the attached drawings, in which:

FIG. 1 is a schematic block diagram embodying the apparatus of the present invention; and FIG. 2 is a schematic circuit diagram of the major portion of the apparatus shown in FIG. 1.

Broadly stated, the apparatus embodying the present invention is preferably adapted for use with a railroad car or the like that is designed and used for detecting flaws in railroad rails and for performing other similar functions relating to maintenance of railroad track and the like. The apparatus of the invention preferably utilizes an ultrasonic transducer mounted in a fluid-filled wheel which is of conventional design and transmits high frequency sound waves into the rail as the car and wheel are travelling along the track. The sound waves are reflected within the rail and the echo signals are detected and forwarded to counting and other circuitry which detects presence of flaws emanating from the bolt hole area as well as other areas of the rail. The high frequency sound wave enters the rail at about 90° relative to horizontal and an echo signal is received by the transducer from the bottom of the rail. Since the echo signal from the bottom of the rail will normally be received in a precisely defined and therefore predetermined time period after the signal enters the rail, only a shorter receipt of the echo signal will indicate that something other than the bottom of the rail caused the signal to be reflected and, presumably, the cause of the reflection will be a discontinuity in the rail, such as a flaw or a bolt hole, for example. In this regard, the echo signal in a typical 133 pound rail will be received in approximately 60 microseconds after the signal enters the rail. If a flaw or a bolt hole is present, the return echo will occur in a shorter time than the 60 microseconds, and the echo from the bottom of the rail will be missing.

The apparatus is adapted to measure the size or horizontal distance of a flaw by correlating the speed of the car with the speed of the pulses fed to a counting circuit and thereby measure the size of flaws that are detected. The apparatus preferably triggers an alarm and recording apparatus in response to the detection of a flaw so that the location thereof can be accurately logged. More specifically, the counter circuit is driven by a pulse generator that has a variable output that is related to the speed of the car and therefore accurately indicates the location of the car along the track. Stated in other words, the pulse generator produces a pulse for every predetermined interval of distance traveled, preferably about 1/16th inch, regardless of the speed the car is moving.

Turning now to the drawings, and particularly the schematic block diagram of FIG. 1, the apparatus includes a pulse generator 10 that has an output that is related to the speed of the car and is operably connected to a car wheel or other take-off in the conventional manner. The pulse generator 10 has its output passing connected by line 11 to a wave squarer and phase converter 12, with the wave squarer being a Schmitt trigger or the like. The output is connected by line 13 to one or more counters 14 which are in turn connected by line 15 to a comparator circuit 16. A second pulse generator 18 which is free-running and therefore independent of the pulse generator 10, is connected through line 19 to drive a transmit and receive transducer 20 which transmits and receives ultrasonic pulses which are applied to the rail through the fluid-filled wheel (not shown) and the echo signal is received thereby. The received echo signal is fed through line 21 to an amplifier and integrator 22 and then through line 23 to a wave squarer, (which also may be a Schmitt trigger or the like) and phase inverter 24 where it is shaped and inverted before being applied through line 25 to one input of a NAND gate 26, the second input of which comes from the pulse generator 18 through line 27, a delay circuit 28 and line 29.

Thus, a pulse generated by the pulse generator 18 is applied to both the transducer 20 and the delay circuit 28 which is preferably adjustable to accommodate differing rail dimensions. If the echo received by the transducer 20 is a reflected signal from the bottom of the rail, indicating that it has traveled the full height of the rail rather than from an intermediate point, the full time period will have elapsed, i.e., the 60 microseconds for the 133 pound rail. If the delay circuit 28 is preset for a 60 microsecond delay, then both inputs of the NAND gate 26 will be satisfied and will produce a reset pulse to the counter 14. It should be similarly understood that if a flaw or bolt hole has caused a pulse to be reflected from an intermediate point in the rail, the reflected pulse will be received in a time period that is less than the 60 microseconds. If this occurs, then the two inputs to the NAND gate 26 will not be simultaneously satisfied and an output reset pulse will not be produced. It should also be understood that the pulses that are transmitted and received by the transducer are not related to the speed or distance traversed by the car on which the apparatus is installed and therefore do not provide an indication of the size of the flaw. The received signal indicates whether the signal has been reflected from either the bottom of the rail, in which case a reset signal is produced, or from an intermediate point, in which case the reset signal is not produced since both inputs to the NAND gate 26 are not simultaneously satisfied.

To provide an indication of the size of the flaw or bolt hole or the like that is detected, the comparators 16 have one input provided by the counters 14 which are driven by the speed related pulse generator 10 and another input provided by variable count presettable switches 32 through line 33. Since the switches 32 have adjustable settings to vary the preset counts, a count slightly larger than the size of bolt holes may be preset so that an alarm and recorder 35 will not be actuated through line 34 unless the count from the counters 14 reaches the count that is preset on the variable count switches, indicating that the bolt hole is oversized or that a fault is present. The speed related pulse generator 10 provides a pulse for an increment of distance traversed by the fluid-filled wheel and preferably provides a pulse for every 1/16th of an inch.

When a bolt hole in the rail is encountered by the apparatus, a reset pulse from the NAND gate 26 will not be generated during the time that the transducer 20 is transmitting and receiving pulses that are reflected by the bolt hole area. Since the reset pulses are not generated, the speed related pulse generator 10 will upcount the counter 14 and it will reach a count that is indicative of the size of the bolt hole. Moreover, the output of the counters 14 are applied to the comparators 16 and the comparators compare the count from the counters 14 against the count from the preset variable count switches 32 so that when the counts are equal, an output is generated to the alarm and recorder 34. Since it is desirable not to provide an alarm and record a flaw for the bolt holes themselves, the variable count switches are preset to be slightly larger than the bolt hole diameters, so that an alarm is not sounded because a reset pulse will be generated before the count of the counters 14 reaches the count from the switches 32. By setting the switches 30 to reflect a slightly oversized diameter, a normal bolt hole will not cause an alarm and only a crack emanating from a bolt hole will be effective in providing an alarm indication as is desired. In this regard, it is preferred that the counters be set about one-eighth inch larger than the bolt hole diameter to allow for minor variations in the bolt hole size to minimize erroneous alarms.

Turning now to the circuit diagram of FIG. 2 which illustrates a portion of the block diagram shown in FIG. 1 relating to the counters, comparators, set switches and alarm indicator, line 13 carries the speed related pulse from the wave squarer and phase inverter 12 to an integrated circuit 36 which comprises six separate inverters. The speed related pulse appearing on line 13 is applied to pin 11 and the corresponding output appears on pin 8 after having gone through two inverters which function as a buffer amplifier, so that the output on pin 8 is in phase with the input applied to pin 11. The clock pulse on pin 8 is fed to a tens counter 14 as well as a units counter 14 which are cascaded together. The reset pulse from NAND gate 26 is also applied through line 31 to pin 5 of the integrated circuit 36 and the inverted output appears on pin 6 thereof which is applied to pin 1 of the units and tens counters 14. The counters 14 are synchronous four bit decade counters that have an asynchronous clear function and the counters are cascaded together so that they count from zero to 99. As previously mentioned, the counters will be reset whenever a reset pulse appears on line 31. Thus, if the apparatus fails to detect a bolt hole, flaw or the like, the counters will be immediately reset and will never advance beyond one, except when a bolt hole or flaw or the like is encountered. The counters 14 have binary coded decimal outputs appearing on pins 11–14 which are respectively connected to pins 15, 13, 12 and 10 of the tens and units comparators 16 which are cascaded together in the conventional manner as shown by the interconnection by lines 38. Units and tens adjustable set switches 32 have their binary coded outputs connected to pins 9, 11, 14 and 1 of the respective comparators so that the count appearing on the counters 14 can be compared to the preset count produced by the binary coded output set switches 32. When the count from the counters 14 equals the preset count of the switches 32, then a positive pulse appears on line 35 which is fed to pin 5 of a monostable multivibrator 40. The output of the monostable multivibrator appears on pin 1 and is in the form of a negative output pulse that is inverted by three parallelled inverter stages of the integrated circuit 36. The resulting positive output pulse drives the base of a transistor 42 which in turn drives a pen coil 44 of a chart recorder (not shown) which records the presence of a flaw. A potentiometer 46 may be provided to control the amplitude of the voltage pulse that is fed to the pen coil.

In addition to providing an alarm and chart recorder to be activated in response to the detection of a flaw or oversized hole, i.e., the absence of a reset pulse over a distance that exceeds the distance that is preset in the switches 32, an exceedingly long flaw or separation of the head web of the rail, for example, may cause the counters to count beyond the maximum count of 99 so that the next speed related pulse will set the counter to zero and the count will begin again. Every time the counter passes the switch setting a pulse will activate the pen coil of the chart recorder and will thereby show that a very long flaw exists.

It should be understood that the integrated circuit components shown in FIG. 2 are standard transistor-transistor-logic components, the numbers of which are standardized and shown in parentheses.

From the foregoing description, an improved detection apparatus has been described that is particularly adapted to detect and record flaws in the bolt hole area of railroad rails, where cracks often originate. The apparatus is effective in its operation and is relatively inexpensive, inasmuch as it can be fabricated using components that are commercially available.

It should be understood that although a preferred embodiment of the present invention has been illustrated and described, various modifications thereof will become apparent to those skilled in the art and, accordingly, the scope of the present invention should be defined only by the appended claims and equivalents thereof.

Various features of the invention are set forth in the following claims.

What is claimed is:

1. Apparatus for moving along a railroad rail to test and detect flaws in the railroad rail, comprising:
    means for transmitting ultrasonic signals into the rail and for receiving associated echo signals reflected from within the rail;
    means operably connected to said transmitting means for producing a trigger signal that causes said transmitting means to transmit an ultrasonic signal, said trigger signal being generated independently of the movement of the apparatus along the rail,
    means operably connected to said trigger signal producing means and said transmitting and receiving means for producing an electrical reset signal only in response to an echo signal being received at a predetermined time following the transmitting of an ultrasonic signal, said predetermined time corresponding to the time at which a transmitted ultrasonic signal which has traveled to and reflected from the bottom of the rail will have returned to the transmitting and receiving means, whereby a reset signal is generated only when an echo signal is received from the bottom of a rail;
    means for producing electrical pulses at predetermined intervals of distance as said apparatus moves along the rail;
    means connected to said pulse producing means and said reset signal producing means for counting said pulses, said counting means being reset in response to a reset signal being received; and
    means sensing the state of said counting means for producing an indication of a flaw when said count exceeds a predetermined value.

2. Apparatus as defined in claim 1 wherein said reset signal producing means includes means for adjusting said predetermined time to accommodate the thickness of the rail or the like being tested.

3. Apparatus for testing and detecting flaws in a railroad rail or the like, comprising:
    means for transmitting ultrasonic signals into the rail and for receiving associated echo signals reflected from within the rail;
    means operably connected to said transmitting means for producing a trigger signal that causes said transmitting means to transmit an ultrasonic signal;
    means operably connected to said trigger signal producing means and said transmitting and receiving means for producing an electrical reset signal only in response to an echo signal being received at a predetermined time following the transmitting of an ultrasonic signal, said predetermined time corresponding to the time at which a transmitted ultrasonic signal which has traveled to and reflected from the bottom of the rail will have returned to the transmitting and receiving means, whereby a reset signal is generated only when an echo signal is received from the bottom of the rail, and including means for adjusting said predetermined time to accommodate the thickness of the rail or the like being tested, said reset signal producing means comprising an adjustable electrical delay circuit having its input connected to the output of said trigger signal producing means and its output connected to the input of a NAND gate and said transmitting means being connected to the other input of said NAND gate whereby simultaneous occurrences of signals at the input to said NAND gate will produce a reset signal at the output thereof;
    means for producing electrical pulses at predetermined intervals of distance as said apparatus moves along the rail;
    means connected to said pulse producing means and said reset signal producing means for counting said pulses, said counting means being reset in response to a reset signal being received; and
    means sensing the state of said counting means for producing an indication of a flaw when said count exceeds a predetermined value.

4. Apparatus as defined in claim 3 further including amplification and wave shaping means interconnected between said transmitting means and said NAND gate input.

5. Apparatus as defined in claim 1 wherein said indication producing means comprises comparator means for comparing the count from the counting means with a preset count appearing on a variable count set switch, said comparator means being adapted to produce an output signal when the count of said counting means reaches the count on the preset switches.

6. Apparatus as defined in claim 1 wherein said electrical pulse producing means is adapted to produce an electrical pulse for each distance of travel of about one-sixteenth inch of said apparatus along the rail.

7. Apparatus for testing and detecting flaws in a railroad rail or the like, comprising:
    transducer means adapted to transmit ultrasonic signals into the rail and receive the echo signals reflected by the rail;
    trigger means for activating said transmitting means, said trigger means operating independently of the movement of the apparatus along the rail;
    gate means operably connected to said transmitting means and to said trigger means for producing a reset signal in the event the echo signal is received after a predetermined time delay;
    means for producing a pulse for each interval of distance of rail over which the apparatus moves;
    counting means connected to said pulse producing means for counting said pulses, said gate means being connected to said counting means and resetting said counting means whenever a reset signal is generated thereby; and
    means connected to said counting means for producing an electrical indicator signal in the event the count reaches a predetermined value.

8. Apparatus as defined in claim 7 including an adjustable delay circuit adapted to change the predetermined time delay to accommodate rails of different heights.

9. Apparatus as defined in claim 8 wherein said delay circuit is preset so that said predetermined time delay approximates the time required for an ultrasonic signal to be transmitted and received through the entire height of the rail.

* * * * *

UNITED STATES PATENT AND TRADEMARK OFFICE
CERTIFICATE OF CORRECTION

PATENT NO. : 4,004,455
DATED : January 25, 1977
INVENTOR(S) : Chester W. McKee and C. Glenn Henderson It is certified that error appears in the above-identified patent and that said Letters Patent are hereby corrected as shown below:

Column 1, line 18 - "are" should be --is--.

Column 1, line 26 - "downwardly and return" should be --down and back--.

Column 1, line 30 - after "length" insert --made--.

Column 1, line 31 - after "in" insert --a--.

Column 1, line 31 - "due to" should be --by--.

Column 1, line 68 - after "detects" insert --the--.

Column 2, line 3 - after "horizontal" insert a comma.

Column 2, line 8 - "a shorter" should be --an earlier--.

Column 2, line 21 - "speed" should be --rate--.

Column 2, line 22 - "measure" should be --measuring--.

Column 2, line 38 - "the" should be --a--.

Column 2, line 40 - omit "passing".

Column 2, line 48 - omit "and receives".

Column 2, line 50 - after "and" insert --receives--.

Column 2, line 50 - omit "is".

Column 2, line 51 - omit "received thereby"

UNITED STATES PATENT AND TRADEMARK OFFICE
CERTIFICATE OF CORRECTION

PATENT NO. : 4,004,455
DATED : January 25, 1977
INVENTOR(S) : Chester W. McKee and C. Glenn Henderson It is certified that error appears in the above-identified patent and that said Letters Patent are hereby corrected as shown below:

Column 2, line 53 - delete the comma.

Column 2, line 65 - after "than" insert --being reflected--.

Signed and Sealed this

Twenty-first Day of June 1977

[SEAL]

Attest:

RUTH C. MASON
Attesting Officer

C. MARSHALL DANN
Commissioner of Patents and Trademarks